(12) United States Patent
Kalloo et al.

(10) Patent No.: US 9,861,444 B2
(45) Date of Patent: Jan. 9, 2018

(54) METHOD AND DEVICE FOR ENDOSCOPIC ABRASION

(71) Applicant: The Johns Hopkins University, Baltimore, MD (US)

(72) Inventors: Anthony N. Kalloo, Baltimore, MD (US); Mouen A. Khashab, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/353,687

(22) PCT Filed: Oct. 30, 2012

(86) PCT No.: PCT/US2012/062571
§ 371 (c)(1),
(2) Date: Apr. 23, 2014

(87) PCT Pub. No.: WO2013/070457
PCT Pub. Date: May 16, 2013

(65) Prior Publication Data
US 2014/0296742 A1    Oct. 2, 2014

Related U.S. Application Data

(60) Provisional application No. 61/554,340, filed on Nov. 1, 2011.

(51) Int. Cl.
| A61B 17/3207 | (2006.01) |
| A61B 19/00 | (2006.01) |
| A61B 10/00 | (2006.01) |
| A61B 17/32 | (2006.01) |
| A61B 10/04 | (2006.01) |
| A61B 90/00 | (2016.01) |
| A61B 17/00 | (2006.01) |

(52) U.S. Cl.
CPC .............. *A61B 19/54* (2013.01); *A61B 10/04* (2013.01); *A61B 17/32002* (2013.01); *A61B 17/320725* (2013.01); *A61B 90/39* (2016.02); *A61B 2017/00557* (2013.01); *A61B 2090/3966* (2016.02)

(58) Field of Classification Search
CPC ............ A61B 17/320725; A61B 10/04; A61B 1/00082
See application file for complete search history.

(56) References Cited

U.S. PATENT DOCUMENTS

| 4,465,072 | A | * | 8/1984 | Taheri | ..................... A61B 17/22 |
| | | | | | 600/569 |
| 5,009,659 | A | * | 4/1991 | Hamlin | .......... A61B 17/320725 |
| | | | | | 30/276 |
| 5,370,653 | A | * | 12/1994 | Cragg | ..................... A61B 17/22 |
| | | | | | 600/569 |

(Continued)

*Primary Examiner* — Michael C Stout
(74) *Attorney, Agent, or Firm* — DLA Piper LLP (US)

(57) ABSTRACT

The present invention provides an endoscopic abrasion device and methods of use thereof. The device includes a catheter having an inflation balloon including one or more elements disposed on the balloon for abrasion of tissue when the balloon is rotated about the longitudinal axis of the catheter. The device may be used to treat and diagnose diseases of the esophageal passage, such as Barrett's disease.

22 Claims, 5 Drawing Sheets

(56) References Cited

U.S. PATENT DOCUMENTS

| | | | |
|---|---|---|---|
| 5,693,014 A | 12/1997 | Abele | |
| 6,096,054 A | 8/2000 | Wyzgala et al. | |
| 6,245,040 B1 | 6/2001 | Inderbitzen et al. | |
| 7,976,564 B2 | 7/2011 | Blaeser et al. | |
| 2003/0208232 A1 | 11/2003 | Blaeser et al. | |
| 2005/0038383 A1* | 2/2005 | Kelley | A61B 17/320725 604/103.06 |
| 2005/0137616 A1* | 6/2005 | Vigil | A61B 17/320725 606/170 |
| 2005/0137617 A1* | 6/2005 | Kelley | A61B 17/320725 606/170 |
| 2006/0015134 A1* | 1/2006 | Trinidad | A61B 17/320725 606/194 |
| 2006/0086701 A1* | 4/2006 | Perreault | B29C 66/80 219/121.64 |
| 2006/0116701 A1* | 6/2006 | Crow | A61B 17/3207 606/159 |
| 2007/0021772 A1* | 1/2007 | von Oepen | A61L 29/06 606/194 |
| 2007/0021774 A1* | 1/2007 | Hogendijk | A61B 17/320758 606/200 |
| 2008/0167678 A1* | 7/2008 | Morsi | A61B 17/320725 606/200 |
| 2008/0195041 A1* | 8/2008 | Goldfarb | A61M 29/02 604/96.01 |
| 2008/0243031 A1* | 10/2008 | Seibel | A61B 1/0008 600/566 |
| 2009/0240270 A1* | 9/2009 | Schneider | A61M 25/104 606/159 |
| 2011/0152683 A1* | 6/2011 | Gerrans | A61B 17/22012 600/435 |
| 2011/0276081 A1* | 11/2011 | Kilemnik | A61B 17/320725 606/198 |
| 2012/0109057 A1* | 5/2012 | Krolik | A61M 25/10 604/103.01 |
| 2012/0289982 A1* | 11/2012 | Gunday | A61B 17/320725 606/159 |
| 2013/0116655 A1* | 5/2013 | Bacino | A61B 17/320725 604/509 |
| 2013/0150874 A1* | 6/2013 | Kassab | A61B 17/320725 606/159 |
| 2013/0267870 A1* | 10/2013 | Lonky | A61B 10/02 600/569 |
| 2013/0317529 A1* | 11/2013 | Golden | A61B 10/0275 606/159 |

* cited by examiner

A  B

A
B

METHOD AND DEVICE FOR ENDOSCOPIC ABRASION

CROSS-REFERENCE TO RELATED APPLICATIONS

This application is a 35 USC §371 National Stage application of International Application No. PCT/US2012/062571 filed Oct. 30, 2012, which claims the benefit under 35 USC §119(e) to U.S. Application Ser. No. 61/554,340 filed Nov. 1, 2011. The disclosure of each of the prior applications is considered part of and is incorporated by reference in the disclosure of this application.

BACKGROUND OF THE INVENTION

Field of the Invention

The invention relates generally to medical devices and more specifically to a device for performing endoscopic abrasion.

Background Information

Barrett's esophagus (BE) is a premalignant condition of the esophagus characterized by columnar metaplasia. The annual rate of progression to esophageal cancer in patients with BE is 0.5% end the life time risk is 5-6%. Endoscopic therapy of BE is currently considered the standard of care. Endoscopic therapeutic modalities include endoscopic mucosal resection, radiofrequency ablation, photodynamic therapy, cryotherapy ablation, and argon plasma coagulation. Endoscopic mucosal resection is the treatment of choice for focal dysplastic nodules; however, radical resection is an unacceptable mode of therapy because of the high incidence of complications (such as esophageal stricture formation in 80% of patients). The remainder of the ablative techniques have suboptimal efficacy (failure to clear dysplasia in 20% of cases; failure to clear BE in 30% of cases; stricture formation in 6% of cases; and buried BE and dysplasia).

Abrasion of the esophageal mucosal layer may be an additional effective therapeutic technique for BE as well as other esophageal mucosal diseases, such as intramucosal adenocarcinoma, intramucosal squamous cell carcinoma, and the like. Accordingly, the art would significantly benefit from availability of a device capable of endoscopic abrasion.

SUMMARY OF THE INVENTION

The present invention provides an endoscopic abrasion device, as well as methods for the treatment of esophageal diseases, such as BE.

Accordingly, in one aspect, the present invention provides an endoscopic abrasion device. The device includes: a) a catheter defining at least one longitudinal lumen, wherein the catheter has a distal end and a proximal end; and b) an inflatable balloon rotatably coupled to the catheter. The balloon has a first configuration with a reduced profile when the balloon in an un-inflated state and a second configuration when the balloon is in an expanded profile. Disposed on the balloon are one or more elements configured to transition from a generally flat configuration when the balloon is in the first configuration, to a generally erect position when the balloon is in the second configuration to facilitate contact with tissue.

In another aspect, the present invention provides a method of treating an esophageal mucosal disease. The method includes: a) advancing the device of the invention into the esophageal cavity of a subject; b) inflating the balloon such that the one or more elements disposed on the balloon are generally erect to facilitate contact with esophageal tissue; and c) actuating the device thereby providing rotation of the balloon and abrasion of the tissue, thereby treating the esophageal mucosal disease. In some embodiments the disease is Barrett's esophagus (BE) or cancer.

In yet another aspect, the present invention provides a method of sampling tissue, such as esophageal tissue. The method includes: a) advancing the device of the invention into the esophageal cavity of a subject; b) inflating the balloon such that the one or more elements disposed on the balloon are generally erect to facilitate contact with tissue; c) actuating the device thereby providing rotation of the balloon and abrasion of the tissue; and d) collecting the abraded tissue, thereby sampling esophageal tissue. The tissue may further be collected and analyzed.

In yet another aspect, the present invention provides a method of diagnosing a condition or disease in a subject. The method includes: a) obtaining a tissue sample from a subject via the method of claim 21; b) analyzing the tissue sample; and c) providing a diagnosis of the condition or disease based on the analysis of (b).

In yet another aspect, the present invention provides a method of providing a prognosis for a condition or disease. The method includes: a) obtaining a tissue sample from a subject via the method of the invention; b) analyzing the tissue sample; and c) providing a prognosis of the condition or disease based on the analysis of (b).

DETAILED DESCRIPTION OF THE INVENTION

The present invention provides an endoscopic abrasion device, as well as methods for the treatment of esophageal diseases, such as BE. Generally, the device utilizes a rotatable balloon that includes elements that facilitate abrasion of esophageal tissue upon rotation of the balloon within the tissue cavity.

The device provides alternative means to treat BE and associated dysplasia. The device of the present invention is feasible to manufacture and the method of its use allows for effective, efficacious, and safe therapy of esophageal disorders. For example, with regard to BE, long segments of BE may be abraded by the device described herein in a relatively short period of time and without the application of electrical current or other types of tissue degrading energies which may potentially avoid procedural-related complications such as stricture formation, perforation, chest pain and the like.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The device of the present invention generally includes: a) a catheter defining at least one longitudinal lumen, wherein the catheter has a distal end and a proximal end; and b) an inflatable balloon rotatably (and preferably water-tightly) coupled to the catheter. In various embodiments, the catheter and balloon are configured for deployment through an endoscope or overtube.

Figure 1:
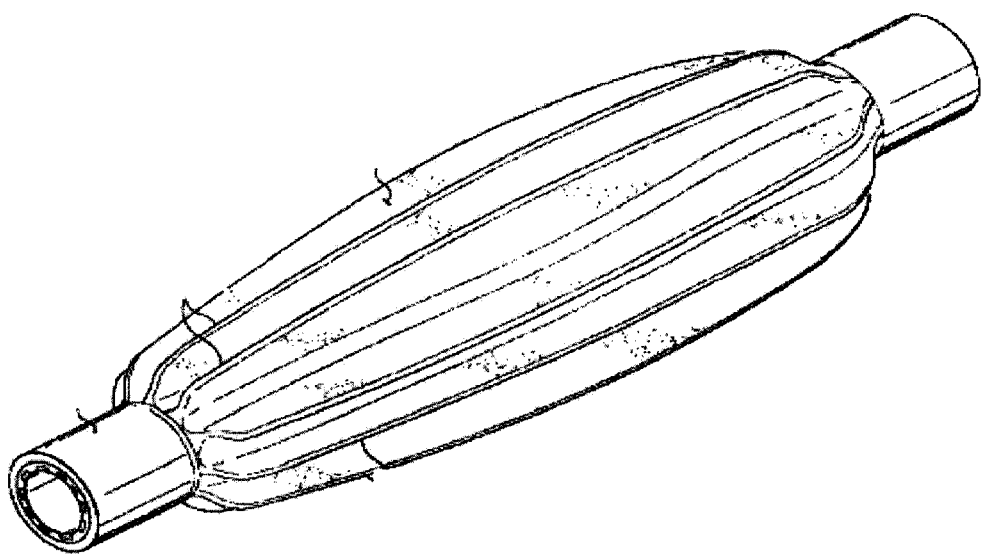
FIG. 1 is a diagram showing an un-inflated catheter balloon having proximal (A) and distal (B) ends in one embodiment of the invention.

By way of illustration, FIG. 1 generally shows the shape of one type of catheter balloon which may be used in the present invention. The balloon is shown in the un-inflated state. The balloon includes both distal (A) and proximal (B) ends with the longitudinal axis running from distal (A) and proximal (B) ends through a center lumen. At least the proximal (B) end may be configured for attachment over a portion of a catheter body. A variety of catheters and balloons are well known in the art and suitable for use with the balloon of the present invention.

Figure 2:
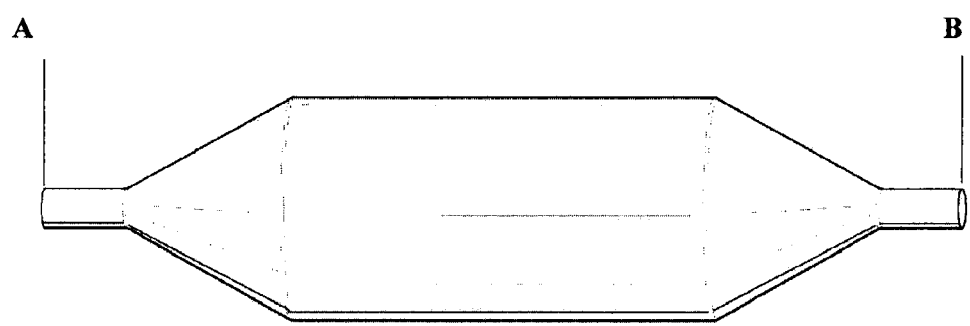
FIG. 2 is a diagram showing an inflated catheter balloon having proximal (A) and distal (B) ends in one embodiment of the invention.

The balloon has a first configuration with a reduced profile when the balloon in an un-inflated state as shown in FIG. 1 and a second configuration when the balloon is in an expanded profile. FIG. 2 generally shows the shape of the catheter balloon of FIG. 1, in an inflated state.

The balloon may be made of a compliant material which resiliently deforms under radial pressure. Examples of suitable compliant materials are generally known in the art and include materials such as, but not limited to polyethylene (PE), polyurethane (PU), nylon, silicone, low density polyethylene (LDPE), polyether block amides (PEBAX), and the like. The balloon may also be made of a semi- or non-compliant material. For example, the balloon may include an inelastic fiber layer and/or sleeve. The inelastic fibers are of high-strength and typically made of a high-strength polymeric material. Examples of suitable materials are generally known in the art and include materials such as, but not limited to Kevlar®, Vectran®, Spectra®, Dacron®, Dyneema®, Terlon® (PBT), Zylon® (PBO), polyimides (PIM), other ultra high molecular weight polyethylene (UHMWPE), aramids, and the like.

Figure 3:
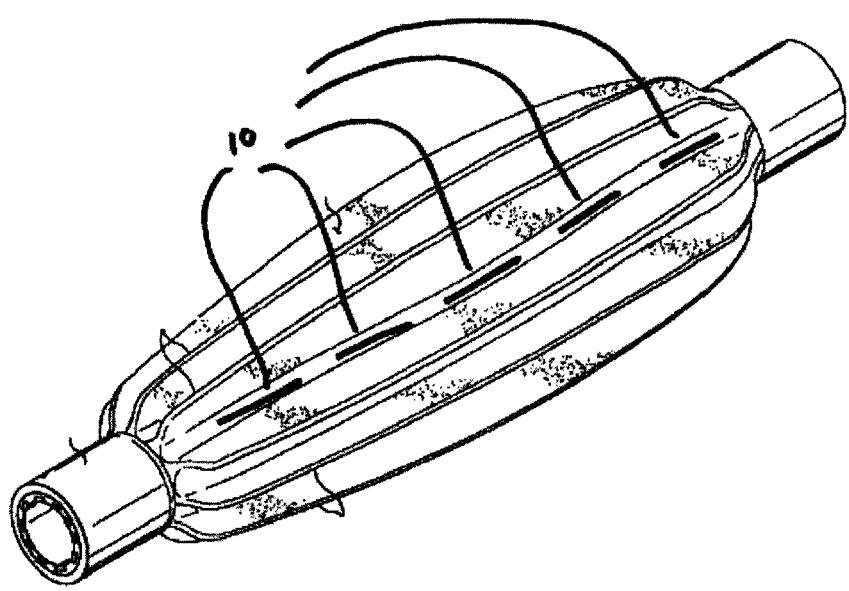
FIG. 3 is a diagram showing an un-inflated catheter balloon having proximal (A) and distal (B) ends including elements 10 in a flat configuration in one embodiment of the invention.
Figure 4:
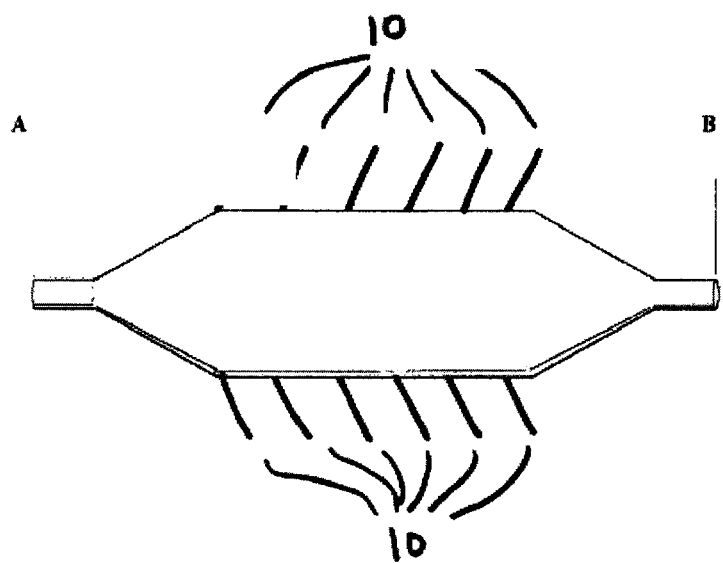
FIG. 4 is a diagram showing an inflated catheter balloon having proximal (A) and distal (B) ends including elements 10 in an erect configuration in one embodiment of the invention.
Figure 5:
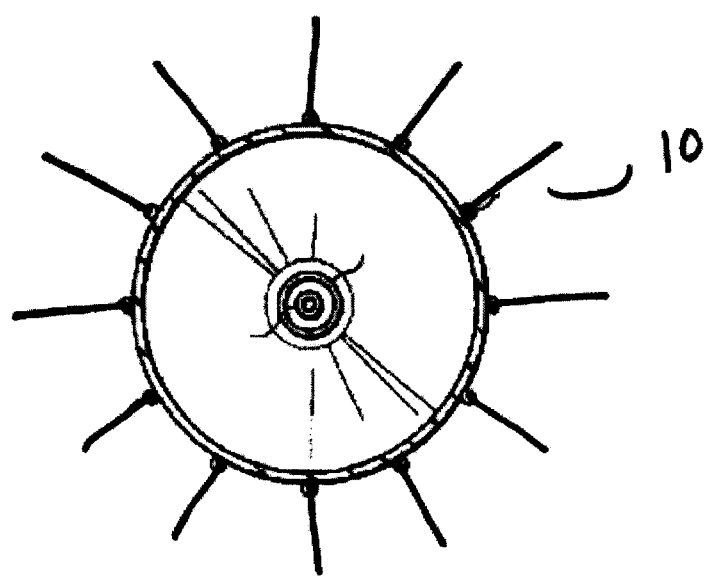
FIG. 5 is a diagram showing a cross-sectional view of an inflated balloon having elements 10 in an erect configuration in one embodiment of the invention.

Disposed on the balloon are one or more abrading elements 10 configured to transition from a generally flat configuration when the balloon is in the first configuration, to a generally erect position when the balloon is in the second configuration to facilitate contact with tissue. FIG. 3 shows a balloon in the un-inflated state with elements 10 being disposed on the surface of the balloon and being generally flat with the surface of the balloon. As the balloon is inflated the elements 10 transition from a generally flat position to an erect position in which the elements project radially from the surface of the balloon as shown in FIG. 4. FIG. 5 shows a cross-sectional view of a balloon in the inflated state having elements 10 in an erect position.

In practice, the device is advanced into the esophageal cavity of a subject. The balloon is then inflated such that the one or more elements 10 disposed on the balloon are generally erect to facilitate contact with esophageal tissue. The balloon is then rotated about the longitudinal axis of the catheter with the cavity to facilitate abrasion of the tissue via elements 10.

In various embodiments, the balloon may be rotated by any means known in the art. By way of illustration, the balloon may be driven by a motor controlled by an actuator, the speed of which may be variably controlled by the operator. Alternatively, the balloon may be rotated manually via a crank shaft and appropriate gears. The speed of the rotation is controllable by the operator. In various embodiments, the balloon is rotated at a speed of about 30, 60, 90, 120, 150, 200, 250, 300, 400, 500 or greater revolutions per minute (RPMs).

It will be understood that elements 10 may be disposed over all or any portion of the balloon in any number of patterns. For example, elements 10 may be disposed in longitudinal stripes along the length of the balloon. Alternatively, elements 10 may be circumferentially disposed on the balloon in a radial fashion. However, any number of patterns may be envisioned.

The balloon may include any number, shape and rigidity of elements 10 that facilitate abrasion of tissue. In some embodiments, elements 10 may be shaped as bristles, teeth, rods, barbs or the like. The elements may range in flexibility and the balloon may include any combination of elements having differing flexibilities. In various embodiments, the balloon may include from about 1 to 5000, 4000, 3000, 2000, 1000 or 500 elements.

One skilled in the art would understand that the device may include any number of balloons disposed along the elongated shaft. For example, 1, 2, 3, 4 or more balloons may be disposed along the catheter, all or some of which may include any number of elements 10.

In various embodiments, the device may further include a radiopaque material. For example, radiopaque material may be incorporated into all or a portion of the balloon to facilitate placement of the balloon within the cavity. Likewise, the radiopaque material may be disposed at the distal tip of the catheter. A variety of radiopaque materials are well known and suitable for use with the present invention. Such materials include, but are not limited to barium, bismuth, tungsten, iridium, iodine, gold, iron, and platinum. A single radiopaque material may be used or such materials may be mixed in various ratios to provide the desired radiopacity.

For diagnostic clinical use, the present invention provides a method of tissue sampling. Therefore, in yet another aspect, the present invention provides a method of sampling tissue. The method includes: a) advancing the device of the invention into a body cavity of a subject; b) inflating the balloon such that the one or more elements disposed on the balloon are generally erect to facilitate contact with tissue; c) actuating the device thereby providing rotation of the balloon and abrasion of the tissue; and d) collecting the abraded tissue, thereby sampling tissue. The tissue sample may further be collected and analyzed for diagnostic, prognostic or research purposes. In various embodiments, the cavity for tissue sample collection is the esophageal cavity.

To facilitate collection of the abraded tissue, a vacuum may be operatively coupled to the catheter. As such, tissue may be collected via a lumen of the catheter.

As used herein, the term "sample" refers to any biological material retrieved from a subject. For example, a sample can be any sample that includes a cell or other biological material that may be utilized for further analysis, including, for example, a tissue, a bodily fluid, or a sample of an organ.

The term "subject" as used herein refers to any individual or patient on or for which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

In various embodiments, the method of the invention further includes analyzing the tissue sample retrieved by the device. One of skill in the art would appreciate that any number of analysis may be performed using the samples to facilitate diagnosis or prognosis of a condition or disorder.

Accordingly, in another aspect, the present invention provides a method of diagnosing a condition or disease in a subject. The method includes: a) obtaining a tissue sample from a subject via the method of the invention; b) analyzing the tissue sample; and c) providing a diagnosis of the condition or disease based on the analysis.

In another aspect, the present invention provides a method of providing a prognosis for a condition or disease in a subject. The method includes: a) obtaining a tissue sample from a subject via the method of the invention; b) analyzing the tissue sample; and c) providing a prognosis of the condition or disease based on the analysis.

As such, the method of the present invention may be used, for example, to evaluate BE and cancer and identify those at risk for cancer based on the results. In any of the methods of diagnosis or prognosis described herein, either the presence or the absence of one or more indicators of cancer, such as, a cancer cell, or of any other disorder, may be used to generate a diagnosis or prognosis.

Samples obtained from a subject may be used to investigate and identify any number of conditions or disorders. As used herein, the terms "condition," "disease," or "disorder" are used to refer to a variety of pathologies. For example, the term may include, but is not limited to, BE and various cancers. The term "cancer" as used herein, includes a variety of cancer types which are well known in the art, including but not limited to, dysplasias, hyperplasias, solid tumors and hematopoietic cancers. Additional cancers may include, but are not limited to, the following organs or systems: brain, cardiac, lung, gastrointestinal, genitourinary tract, liver, bone, nervous system, gynecological, hematologic, skin, breast, and adrenal glands. Additional types of cancer cells include gliomas (Schwannoma, glioblastoma, astrocytoma), neuroblastoma, pheochromocytoma, paraganlioma, meningioma, adrenalcortical carcinoma, medulloblastoma, rhabdomyoscarcoma, kidney cancer, vascular cancer of various types, osteoblastic osteocarcinoma, prostate cancer, ovarian cancer, uterine leiomyomas, salivary gland cancer, choroid plexus carcinoma, mammary cancer, pancreatic cancer, colon cancer, and megakaryoblastic leukemia; and skin cancers including malignant melanoma, basal cell carcinoma, squamous cell carcinoma, Karposi's sarcoma, moles dysplastic nevi, lipoma, angioma, dermatofibroma, keloids, sarcomas such as fibrosarcoma or hemangiosarcoma, and melanoma.

Once obtained, a sample is typically further processed and analyzed. Processing of the sample may include isolation of a biological component of the sample, such as a protein, a nucleic acid molecule, or individual cell. In some embodiments, the sample is processed to isolate nucleic acids, such as DNA and RNA. In some embodiments, the sample is processed to isolate individual cells.

The term "nucleic acid molecule" is used broadly herein to mean a sequence of deoxyribonucleotides or ribonucleotides that are linked together by a phosphodiester bond. As such, the term "nucleic acid molecule" is meant to include DNA and RNA, which can be single stranded or double stranded, as well as DNA/RNA hybrids. Furthermore, the term "nucleic acid molecule" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR), and, in various embodiments, can contain nucleotide analogs or a backbone bond other than a phosphodiester bond.

The terms "polynucleotide" and "oligonucleotide" also are used herein to refer to nucleic acid molecules. Although no specific distinction from each other or from "nucleic acid molecule" is intended by the use of these terms, the term "polynucleotide" is used generally in reference to a nucleic acid molecule that encodes a polypeptide, or a peptide portion thereof, whereas the term "oligonucleotide" is used generally in reference to a nucleotide sequence useful as a probe, a PCR primer, an antisense molecule, or the like. Of course, it will be recognized that an "oligonucleotide" also can encode a peptide. As such, the different terms are used primarily for convenience of discussion.

In various embodiments, a sample may be analyzed in a variety of ways to identify a condition or disorder. Typically, the analysis include investigation of one or more nucleic acid molecules to diagnose a disease or condition, e.g., genetic analysis. In some embodiments, a sample may be analyzed by performing image analysis of individual cells to, for example, characterize cell type and cell morphology. Detectable markers, such as cell surface markers and nuclear markers, cell type, cell size, cell shape and the like may be analyzed using various microscopy and imaging techniques known in the art.

As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule.

Any number of analyses may also be performed of the sample or component thereof, to provide clinical assessment. For example, gene expression analysis and PCR techniques may be employed, such as gene chip analysis and multiplexing with primers specific for particular markers to obtain information such as the type of a tumor, metastatic state, and degree of malignancy. In some embodiments, expression of individual genes associated with a disease or disorder is examined. In some embodiments, expression of cell surface markers may be analyzed. As used herein, "expression" refers to the production of a material or substance as well as the level or amount of production of a material or substance. Thus, determining the expression of a specific marker refers to detecting either the relative or absolute amount of the marker that is expressed or simply detecting the presence or absence of the marker.

Additionally, cell size, DNA or RNA analysis, proteome analysis, or metabolome analysis may be performed as a means of assessing additional information regarding characterization of a disease or disorder. In various aspects, analysis may include antibodies directed to or PCR multiplexing using primers specific for one or more of markers. Examples of well known cancer markers include: EGFR, HER2, ERCC1, CXCR4, EpCAM, E-Cadherin, Mucin-1, Cytokeratin, PSA, PSMA, RRM1, Androgen Receptor, Estrogen Receptor, Progesterone Receptor, IGF1, cMET, EML4, and Leukocyte Associated Receptor (LAR).

Analysis may also include performing methylome analysis or detecting the methylation status of an isolated nucleic acid molecule. In various embodiments, the determining of methylation status is performed by one or more techniques selected from a nucleic acid amplification, polymerase chain reaction (PCR), methylation specific PCR, bisulfite pyrosequenceing, single-strand conformation polymorphism (SSCP) analysis, restriction analysis, microarray technology, and proteomics. Analysis of methylation can be performed by bisulfite genomic sequencing. Bisulfite treatment modifies DNA converting unmethylated, but not methylated, cytosines to uracil. Bisulfite treatment can be carried out using the METHYLEASY™ bisulfite modification kit (Human Genetic Signatures). Other methods are known in the art for determining methylation status, including, array-based methylation analysis, Southern blot analysis, molecular beacon technology, Taqman™ technology, methyl light, Methyl Heavy, or SNuPE (single nucleotide primer extension). The degree of methylation in a nucleic acid molecule may also be measured by fluorescent in situ hybridization (FISH).

With regard to cancer, analysis allows for meaningful characterization useful in assessing diseases prognosis and in monitoring therapeutic efficacy for early detection of treatment failure that may lead to disease relapse. In addition, analysis may enable the detection of early relapse in pre-symptomatic patients who have completed a course of therapy. Thus, enumeration and characterization of specific cells of a sample provides methods to stratify patients for baseline characteristics that predict initial risk and subsequent risk based upon response to therapy.

In various aspects, samples may be obtained and analyzed over a particular time course in various intervals to assess a subject's progression and pathology. For example, analysis may be performed at regular intervals such as one day, two days, three days, one week, two weeks, one month, two months, three months, six months, or one year.

Analysis may provide data sufficient to make determinations of responsiveness of a subject to a particular therapeutic regime, or for determining the effectiveness of a candidate agent in the treatment of a disease or disorder, such as cancer. For example, once a drug treatment is administered to a patient, it is possible to determine the efficacy of the drug treatment using the method of the invention. For example, a sample taken from the patient before the drug treatment, as well as one or more cellular samples taken from the patient concurrently with or subsequent to the drug treatment, may be isolated and processed using the method of the invention. By comparing the results of the analysis of each processed sample, one may determine the efficacy of the drug treatment or the responsiveness of the patient to the agent. In this manner, early identification may be made of failed compounds or early validation may be made of promising compounds.

Although the invention has been described with reference to the above example, it will be understood that modifications and variations are encompassed within the spirit and scope of the invention. Accordingly, the invention is limited only by the following claims.

What is claimed is:

1. An endoscopic abrasion device, comprising:
    a) a catheter defining at least one longitudinal lumen extending along a longitudinal axis of the catheter, wherein the catheter has a distal end and a proximal end;
    b) an inflatable balloon rotatably coupled to the distal end of the catheter, the balloon having a first configuration with a reduced profile when the balloon in an uninflated state and a second configuration when the balloon is in an expanded profile, the balloon comprising a plurality of elongated elements having a length disposed on the balloon configured to abrade biological tissue, the plurality of elongated elements spaced along the longitudinal axis of the catheter, the plurality of elongated elements being configured to transition from a generally flat configuration in which that the plurality of elongated elements are generally flat with an external surface of the balloon when the balloon is in the first configuration, to a generally erect position in which the plurality of elongated elements project radially from the surface of the balloon to radially disposed tips when the balloon is in the second configuration, wherein the length of the plurality of elongated elements is aligned along the longitudinal axis of the catheter in the first configuration and the second configuration, wherein the plurality of elongated elements remain exposed on the external surface of the balloon in the first configuration and the second configuration, and wherein the radially disposed tips are oriented toward the proximal end of the catheter in the first configuration and the second configuration;
    c) an actuator operable to rotate the inflatable balloon about the longitudinal axis of the catheter to facilitate abrasion of surrounding tissue by the one or more elements; and
    d) a vacuum operatively coupled to the catheter configured to collect abraded tissue through a lumen of the catheter.

2. The device of claim 1, wherein the plurality of elements are configured as bristles, barbs, rods, or teeth.

3. The device of claim 1, wherein the balloon comprised between 2 to 1000 elements.

4. The device of claim 1, wherein the plurality of elements are disposed in a striped pattern along the length of the balloon.

5. The device of claim 1, wherein the plurality of elements are disposed circumferentially around the balloon.

6. The device of claim 1, wherein the balloon further comprises a radiopaque material.

7. The device of claim 6, wherein the radiopaque material is selected from the group of materials consisting of powdered tungsten, gold, iridium, platinum, barium, bismuth, iodine or iron.

8. The device of claim 1, wherein the balloon comprises a wall having proximal and distal portions and having interior and exterior surfaces, the interior surface of the balloon wall being secured to the catheter in a fluid-tight manner.

9. The device of claim 1, wherein the catheter further comprises an inflation lumen in fluid communication with the balloon whereby fluid or gas can be infused and withdrawn to inflate and to deflate the balloon.

10. The device of claim 1, wherein the actuator is configured to rotate the balloon at between about 10 to 2500 rpms.

11. A method of treating an esophageal mucosal disease, comprising:
    a) advancing the device of claim 1 into the esophageal cavity of a subject;
    b) inflating the balloon such that the plurality of elements disposed on the balloon are generally erect to facilitate contact with esophageal tissue; and
    c) actuating the device thereby providing rotation of the balloon and abrasion of the tissue, thereby treating the esophageal mucosal disease.

12. The method of claim 11, wherein the disease is selected from Barrett's esophagus (BE) or cancer.

13. The method of claim 12, wherein the cancer is a carcinoma.

14. The method of claim 13, wherein the cancer is selected from adenocarcinoma or squamous cell carcinoma.

15. The method of claim 11, further comprising tissue resection, tissue ablation, or a combination thereof.

16. The method of claim 11, further comprising collecting abraded tissue.

17. The method of claim 11, wherein the abraded tissue is collected by applying a vacuum to the lumen of the catheter to facilitate collection of the tissue from one or more opening disposed at the distal end of the device.

18. A method of sampling esophageal tissue comprising:
    a) advancing the device of claim 1 into the esophageal cavity of a subject;
    b) inflating the balloon such that the plurality of elements disposed on the balloon are generally erect to facilitate contact with esophageal tissue;
    c) actuating the device thereby providing rotation of the balloon and abrasion of the tissue; and
    d) collecting the abraded tissue, thereby sampling esophageal tissue.

19. The method of claim 18, further comprising analyzing the collected tissue.

20. The method of claim 19, wherein the analysis comprises analysis of one or more nucleic acid sequences.

21. A method of diagnosing a condition or disease in a subject comprising:
    a) obtaining a tissue sample from a subject via the method of claim 18;
    b) analyzing the tissue sample; and
    c) providing a diagnosis of the condition or disease based on the analysis of (b).

22. A method of providing a prognosis for a condition or disease in a subject comprising:
    a) obtaining a tissue sample from a subject via the method of claim 18;
    b) analyzing the tissue sample; and
    c) providing a prognosis of the condition or disease based on the analysis of (b).

* * * * *